(12) United States Patent
Schmied et al.

(10) Patent No.: US 8,734,449 B2
(45) Date of Patent: May 27, 2014

(54) MEDICAL OR SURGICAL HANDPIECE

(75) Inventors: Walter Schmied, Ostermiething (AT); Manfred Kainhofer, Wals-Siezenheim (AT)

(73) Assignee: Arthrex, Inc., Naples, FL (US)

( * ) Notice: Subject to any disclaimer, the term of this patent is extended or adjusted under 35 U.S.C. 154(b) by 905 days.

(21) Appl. No.: 12/756,945

(22) Filed: Apr. 8, 2010

(65) Prior Publication Data
US 2010/0262127 A1    Oct. 14, 2010

(30) Foreign Application Priority Data

Apr. 9, 2009 (EP) .................................. 09005189

(51) Int. Cl.
*A61B 17/32* (2006.01)

(52) U.S. Cl.
USPC ............................................................ 606/80

(58) Field of Classification Search
CPC ........... A61B 17/1622; A61B 17/1624; A61B 17/1628
USPC .............. 408/36; 173/48, 164, 178, 197, 213, 173/214, 216, 217; 30/38, 392–394, 30/205–210, 215–220, 263, 264, 277.4, 30/381–383; 606/26, 94, 104, 79–82, 180; 310/40 MM, 50, 75 R; 81/57, 57.11, 81/57.31
See application file for complete search history.

(56) References Cited

U.S. PATENT DOCUMENTS

| | | | | |
|---|---|---|---|---|
| 2,838,962 A * | 6/1958 | Curtis | ............................ | 408/36 |
| 4,050,528 A * | 9/1977 | Foltz et al. | .................... | 173/217 |
| 4,109,735 A * | 8/1978 | Bent | ............................. | 173/221 |
| 4,436,168 A * | 3/1984 | Dismukes | ........................ | 175/94 |
| 5,207,697 A * | 5/1993 | Carusillo et al. | ............. | 606/167 |
| 7,098,563 B2 * | 8/2006 | Yang | ............................... | 310/83 |

FOREIGN PATENT DOCUMENTS

DE          36 39 696          6/1988

OTHER PUBLICATIONS

European Search Report for EP09005189 (mailed Sep. 22, 2009).

* cited by examiner

*Primary Examiner* — Todd Manahan
*Assistant Examiner* — Eric S Gibson
(74) *Attorney, Agent, or Firm* — Dickstein Shapiro LLP

(57) ABSTRACT

A medical or surgical handpiece for driving a medical tool comprises a housing, a drive train accommodated therein and a motor. The motor includes a first drive shaft and a second shaft, the second shaft being at least partially arranged in the first drive shaft and mounted to rotate freely relative to the first drive shaft via at least one bearing, so that the second shaft is rotatable independently of the first shaft.

16 Claims, 4 Drawing Sheets

MEDICAL OR SURGICAL HANDPIECE

CROSS REFERENCE TO RELATED APPLICATION

The present applications claims priority from pending European Patent Application No. 09005189.7 filed Apr. 9, 2009, which is incorporated herein by reference.

BACKGROUND

1. Field

The present invention relates to a medical handpiece, including a surgical handpiece, for driving a medical tool.

2. Description of Prior Art

Such medical or surgical handpieces serve to drive medical tools, e.g., saws, drills or surgical drill wires. To do so, the tools are attached to the handpiece by coupling devices. A plurality of different tools can therefore be operated by using one handpiece.

Surgical drill wires are used for treating fractures in surgery. In this procedure, the drill wires are rotated, preferably by a driven handpiece, and drilled into the bone material. By repeating the sequence "drilling into the bone material, releasing the chucking device, resetting the handpiece, renewed chucking of the wire and drilling" several times, the drill wire can be introduced into the bone material easily by using the handpiece and without applying much force.

To be able to design the length of these surgical drill wires independently of the driven handpieces, in particular the chucking devices holding the wire, the handpieces provided for this application are provided with through-bores for the wire, extending through the interior of the handpiece. Drill wires of any length may thus be accommodated in the chucking device and driven by means of a drive, preferably to rotate or to oscillate.

U.S. Pat. No. 5,207,697 describes such a medical or surgical handpiece for holding a surgical drill wire in the interior of the handpiece, in particular in its drive train.

This known surgical handpiece for introducing drill wires into bone material has a handpiece housing with an electric drive accommodated therein, having a first drive shaft and a first drive rotational speed. This first shaft is connected by a gear to a second output shaft arranged coaxially with the first shaft. This shaft, rotating at a second, lower output rotational speed, serves to drive a coupling device for a surgical tool that can be attached to the handpiece, in particular for a surgical drill wire. A second housing opening coaxial with the two shafts of the drive train for insertion of a wire through the shaft configuration to accommodate the wire in the coupling device is provided on the opposite side of the receptacle opening for the coupling device. Because of the different rotational speeds of the multiple shafts of the drive train, there has been abrasion in the past, leading to breakage of the drill wire. To avoid this abrasion of the drill wire, the output shaft according to the present document is lengthened by means of a third shaft extending through the drive shaft. This ensures that only one output rotational speed, namely that of the second and third shafts, which are joined together, acts on the drill wire through the entire handpiece.

One disadvantage of this design of the handpiece for driving a medical tool, in particular a surgical drill wire, has proven to be the dependence of the rotational speed acting on the wire on the shaft configuration of the drive train. The rotational speed of the shaft configuration guiding the drill wire through the handpiece, namely the interconnected second and third shafts, is determined by the motor in the handpiece and its gear. If different tools are connected to the handpiece, as indicated above, this necessitates different drive rotational speeds. The respective coupling devices belonging to the tools therefore have additional gear configurations to adapt the output rotational speed of the handpiece to the predetermined drive rotational speed of the tools. Consequently, there is another rotational speed difference that is not taken into account in the prior art, namely the difference between the output rotational speed of the handpiece and the drive rotational speed of the coupling device. This again results in damage to the drill wire.

Another disadvantage of the embodiment known in the prior art is the lack of bearing support of the third shaft. Due to the arrangement of the third and/or lengthened second shaft in the drive shaft without additional bearing support with respect to the drive shaft, the result is merely a displacement from abrasion on the drill wire to abrasion on the third shaft. By inserting the drill wire through the shaft configuration, in particular through the third shaft, into the coupling device and resetting the handpiece in drilling the wire into the bone material and also because of the inherent imbalance of the wire in the driven state, contact between the first and third shafts which are arranged one inside the other and driven at two different rotational speeds is unavoidable without separate bearing of the third shaft. This ultimately leads to increased wear on the third shaft.

SUMMARY

According to one aspect, the present medical or surgical handpiece allows a tool, in particular a drill wire, to be accommodated in the drive train of a handpiece without damaging the drill wire due to the differences in rotational speed that occur within the drive train. In addition, accommodation of a tool in a handpiece is to be made possible, in particular in its drive train independently of the handpiece and independently of the rotational speed in particular.

According to one exemplary embodiment of a medical or surgical handpiece for driving a medical tool, it has a housing, a drive train accommodated therein, comprising a motor, a first drive shaft and a second drive shaft, the second drive shaft being arranged at least partially in the first drive shaft and being mounted to rotate freely relative to the first drive shaft by means of at least one bearing, so that the second shaft is rotatable independently of the first shaft.

A drive train having a motor, preferably an electric motor with a drive shaft, is provided in the present medical or surgical handpiece. To accommodate drill wires of any length in a coupling device which is connectable or fixedly attached to the handpiece, the drive train has a through-bore passing through the handpiece. This is preferably embodied by at least one tubular shaft in the drive train and by a housing opening arranged coaxially with the drive shaft on the rear side of the handpiece. To accommodate and allow the passage of drill wires through the rotating shaft configuration without damage to the wire, the present drive train has a second shaft mounted to rotate freely relative to the first drive shaft and to rotate independently of the first drive shaft. Due to the bearing support of the second shaft by means of at least one bearing with respect to the drive train, in particular with respect to a drive shaft or a rotationally fixed component of the handpiece, the second shaft is accommodated in the drive train without being driven and is not driven by the motor and/or its gear unit and is thus able to rotate freely with respect to the drive shaft.

With an arrangement of a gear unit in the drive train of the handpiece, the drive shaft is preferably designed in two parts as a motor shaft and as a first output shaft. In addition, a second output shaft may be driven by the drive shaft via the gear. To accommodate a tool in the drive train independently of the rotational speed of the handpiece, the second, freely rotatable drive shaft extends through the motor shaft and the first output shaft and/or the second output shaft.

For the bearing support of the second shaft so it is freely rotatable in the drive train, the shaft is supported by at least one bearing, in particular a roller bearing, on a recess of a shaft wall of a tubular shaft of the drive train or a rotationally fixed component of the handpiece, in particular on a housing opening arranged coaxially with the drive train.

To transmit the drive movement from the motor of the handpiece to the drill wire, the handpiece also has a coupling device which is connectable or is fixedly attached to the drive train, particularly to the first or second output shaft, and has a coupling shaft. The coupling device may be designed with a second gear unit to adjust the output rotational speed of the handpiece to the drive rotational speed of the respective tool. In the case of a coupling device fixedly attached to the drive train, the second shaft holding the drill wire may extend at least partially through the coupling shaft. In the case of a coupling device detectable from the drive train, the second shaft is preferably designed in several parts, in particular in two parts for bearing support in the drive shaft and/or the output shaft as well as in the coupling shaft.

The present medical or surgical handpiece offers a number of substantial advantages, some of which may include the following.

Due to the bearing support of a second shaft which is mounted to rotate freely relative to a first drive shaft of a drive train, a handpiece, in particular for drill wires, is created, allowing a drill wire to be held and to be passed through the shaft configuration of the handpiece independently of the rotational speed of the drive train. The rotational speed independent passage of the handpiece ensures the coupling of a wide variety of coupling devices with different drive rotational speeds, without resulting in a difference in rotational speed between the output rotational speed of the handpiece and the drive rotational speed of a coupling device, preferably detachable.

Another advantage involves the support of the second shaft with respect to the drive shaft by means of a bearing, particularly of a roller bearing. Contact between the second shaft and the drive shaft is prevented by the bearing support within the drive shaft and/or with respect to a rotationally fixed component of the handpiece, such as that which may occur, for example, due to the insertion of the drill wire through the second shaft into the coupling device and in resetting of the handpiece in drilling the wire into the bone material and also due to the inherent imbalance of the wire in the driven state. Wear on the shaft due to possible differences in rotational speed and the resulting friction are thus prevented.

Within the scope of the present application, it is of course self-evident that the medical or surgical handpiece is not limited to handpieces through which surgical drill wires are passed. The handpiece may be used in a variety of medical tools.

These and other embodiments are explained in greater detail below in conjunction with the accompanying drawings.

DETAILED DESCRIPTION

Figure 1:
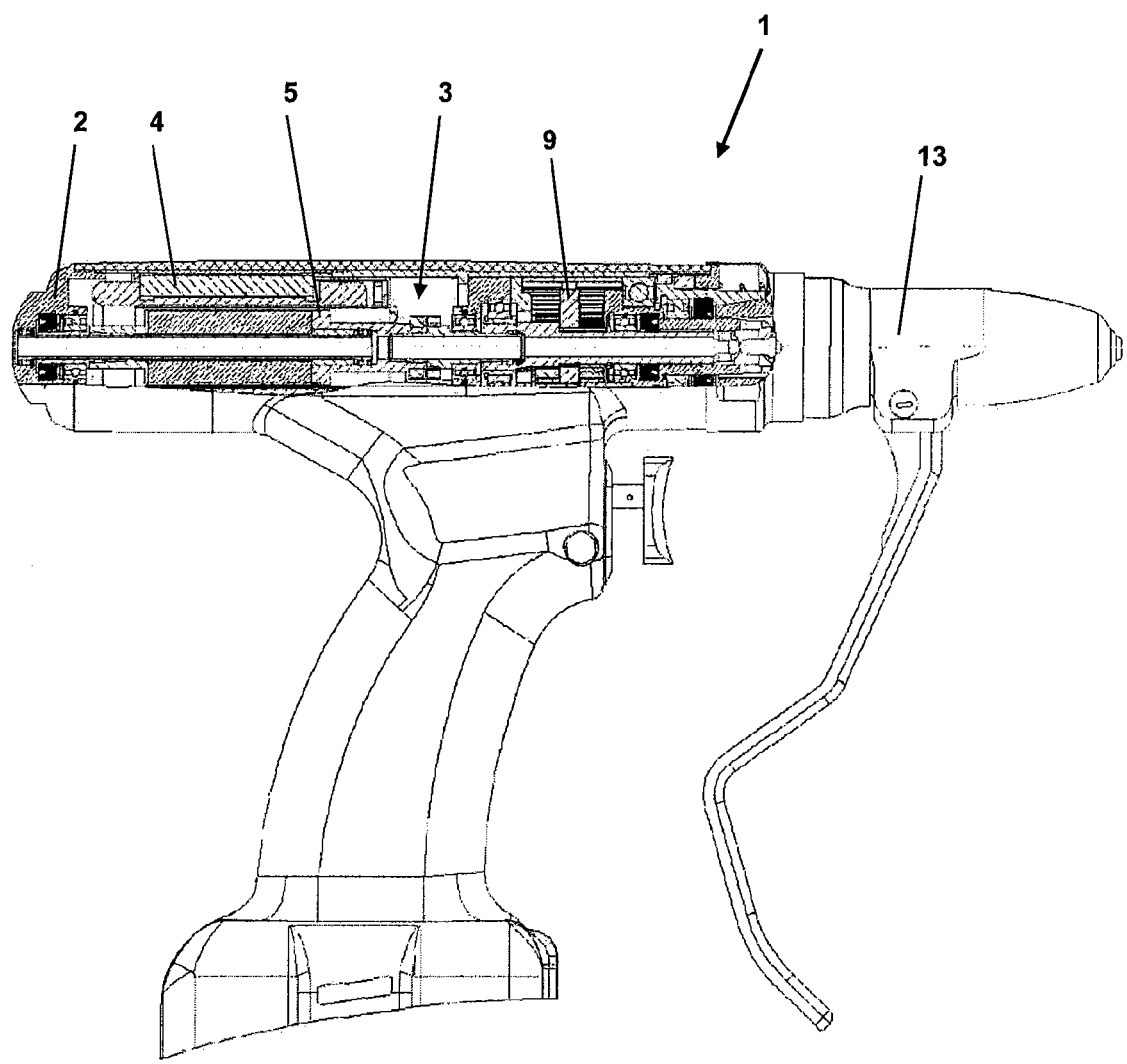
FIG. 1 shows a longitudinal section through the medical or surgical handpiece.

The medical or surgical handpiece 1 shown in FIG. 1 is designed as a pistol-shaped instrument having a coupling device 13, which is connectable or fixedly attached thereto. A drive train 3 for driving a tool by means of a coupling device 13 is arranged in the housing 2 of the handpiece 1. The drive train 3 comprises at least one motor 4, in particular an electric motor or an air motor, and a first drive shaft 5. In addition, the drive train 3 may have a gear 9.

Figure 2:
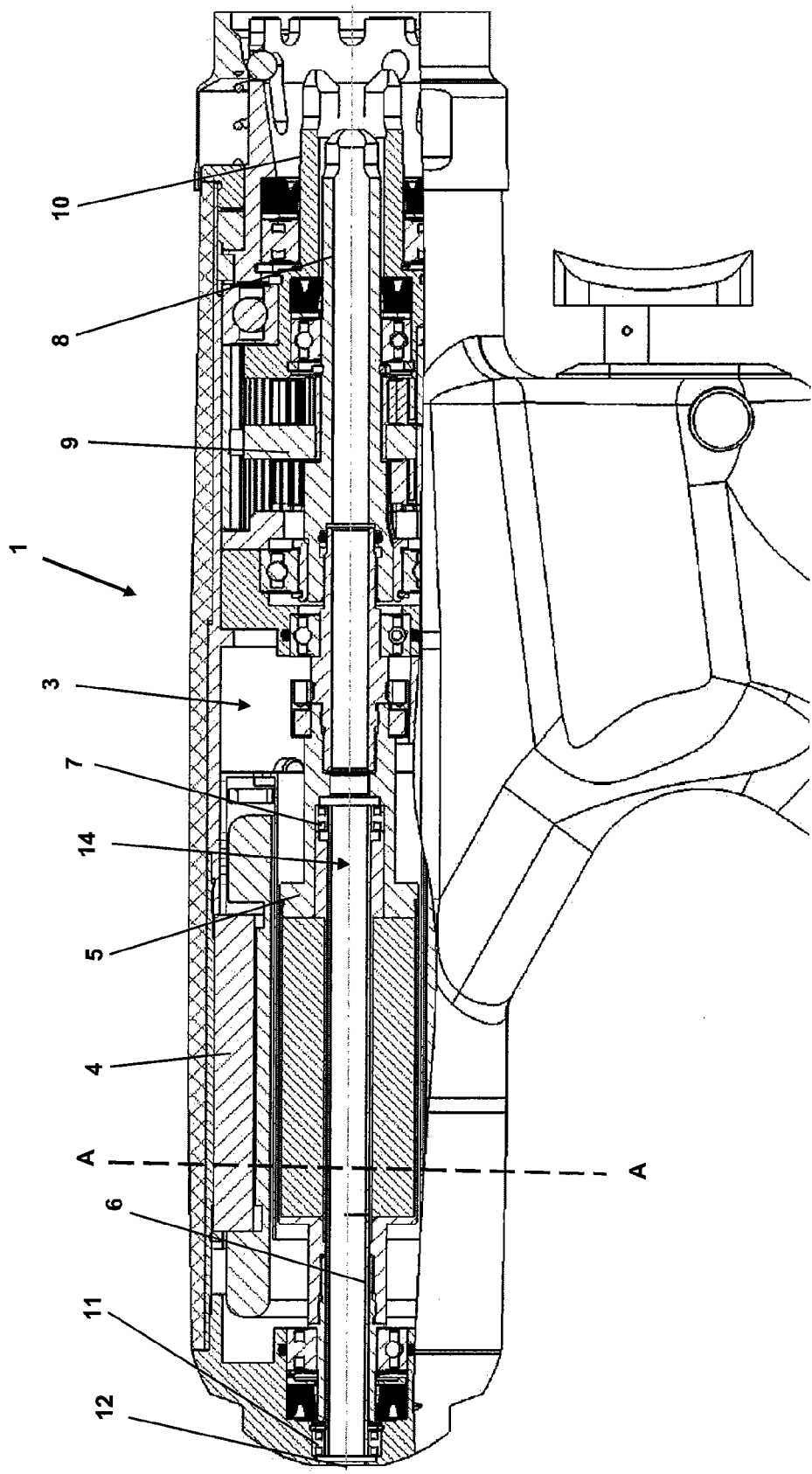
FIG. 2 shows a longitudinal section through a first embodiment of the drive train of the medical or surgical handpiece.

FIG. 2 shows the drive train 3 in the housing 2 of the handpiece 1. The motor 4 and its motor shaft 5 drive a first output shaft 8 and a second output shaft 10 via a gear 9. To accommodate a drill wire of any length and pass it through the drive train 3 of the handpiece 1 without damaging it due to possible differences in the rotational speeds of the multiple shafts, a second shaft 6 is mounted so it can rotate freely relative to the first drive shaft 5 by means of the bearings 7 and 11, so that the second shaft 6 is rotatable independently of the first shaft 5. A housing opening 12, which is coaxial with the tubular shaft configuration of the drive train 3, is situated on the rear end of the handpiece 1, forming together therewith a through-bore 14 passing through the handpiece 1. The bearings 7 and 11 are designed as roller bearings in particular, preferably as ball bearings, and are mounted in the drive train 3 or on a rotationally fixed component of the handpiece 1. To this end, the bearings 7 and 11 are preferably accommodated on one end of the drive train 3 or on a shaft part of the drive train 3, preferably by means of a recess in the shaft wall, or they are accommodated in a housing opening 12 arranged coaxially with the drive train 3.

Figure 3:
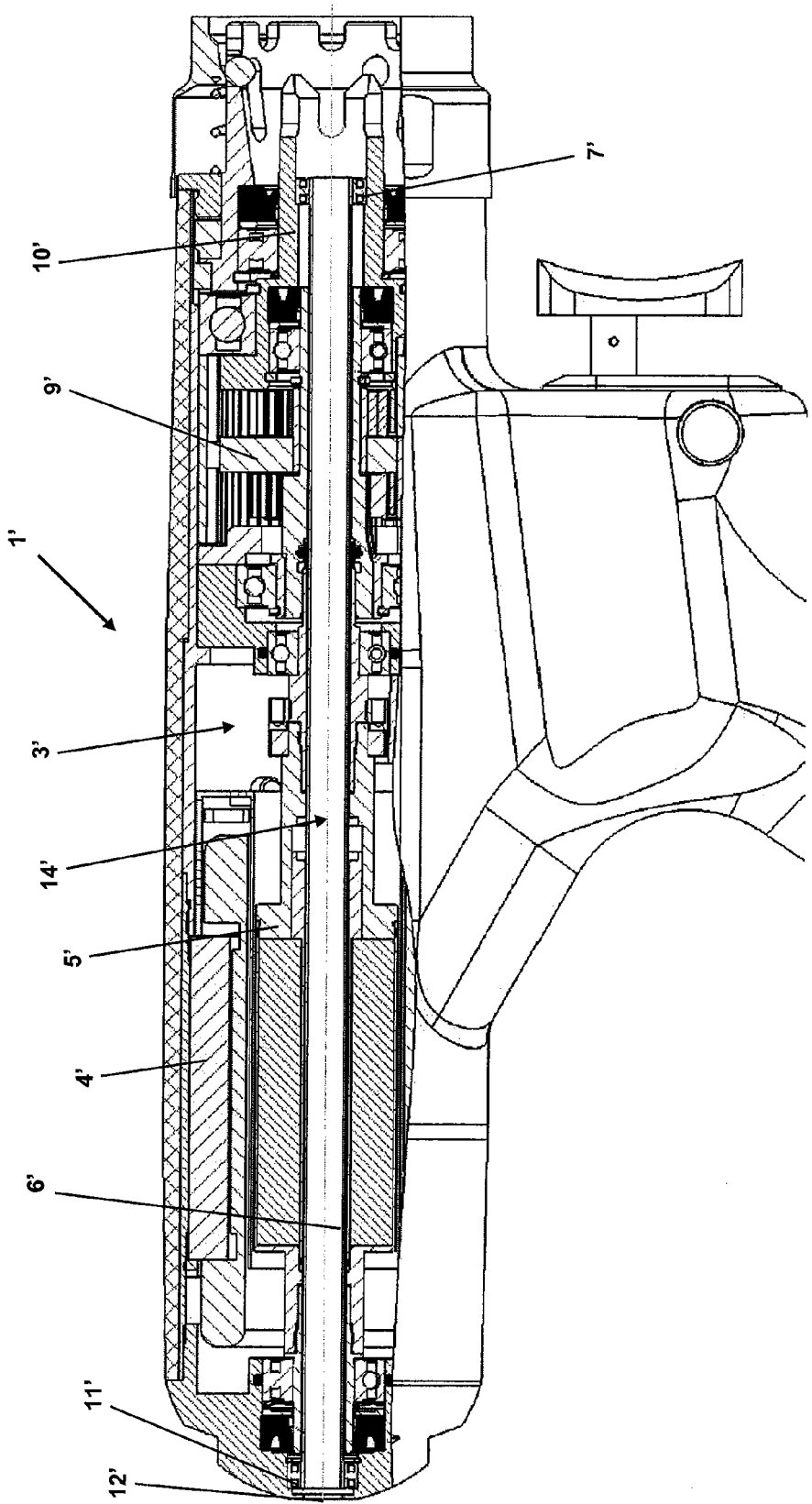
FIG. 3 shows a longitudinal section through a second embodiment of the drive train of the medical or surgical handpiece.

FIG. 3 shows an alternative embodiment of the drive train and the arrangement and bearing support of the second shaft in the handpiece. A motor shaft 5' is driven by the motor 4' in the drive train 3'. This shaft 5' drives an output shaft 10' via a gear 9'. In this embodiment of the drive train 3', the second shaft 6' extends through the drive shaft 5' and the output shaft 10'. Due to the bearing support of the second shaft 6' by means of the bearing 7' against a recess in the shaft wall of the output shaft 10' and of the bearing 11' with respect to a rotationally fixed component of the handpiece 1', the second shaft 6' is mounted to be freely rotatable relative to the drive shaft 5' and the output shaft 10', so that the second shaft 6' is rotatable independently of the drive shaft 5' and the output shaft 10'. The through-bore 14' passing through the handpiece 1' and the housing opening 12' thus allow a drill wire to be accommodated and passed through the drive train 3' independently of the handpiece and in particular independently of the rotational speed.

Figure 4:
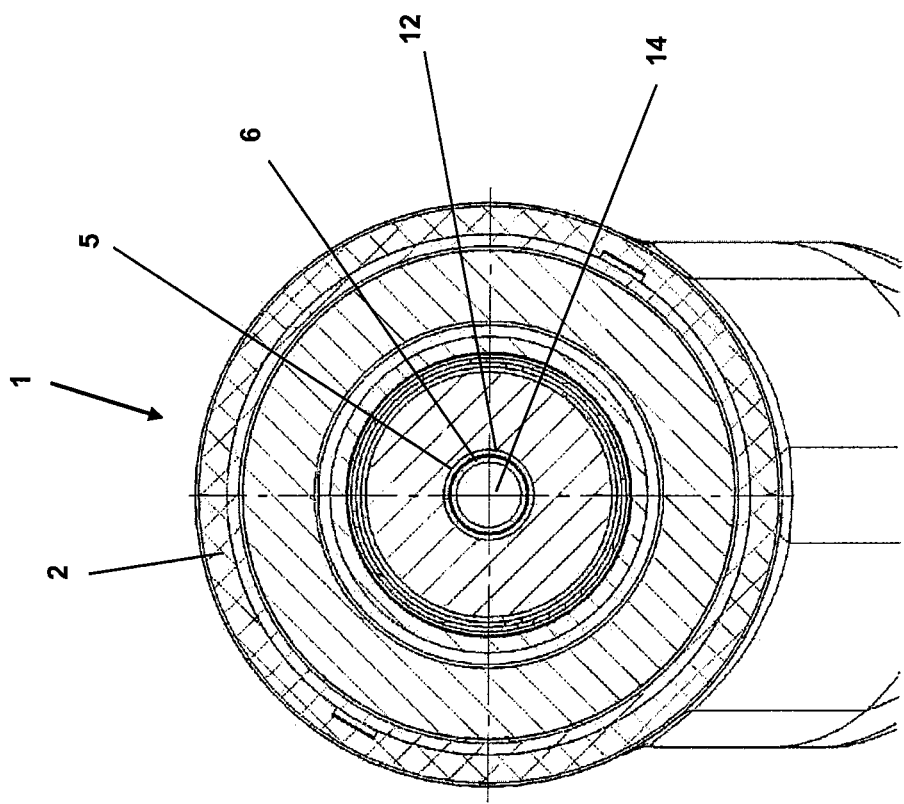
FIG. 4 shows a cross section through the medical or surgical handpiece.

FIG. 4 shows a cross section through the handpiece 1 along line A-A in FIG. 2. A drive train with its drive shaft 5 is arranged in the housing 2 of the handpiece 1. The second freely rotatable shaft 6 is mounted in the drive shaft 5. This shaft, in particular this tubular shaft, together with the housing opening 12 forms a central through-bore 14 for a tool, in particular for a drill wire, through the handpiece 1.

The present application is not limited in scope to the exemplary embodiments described here, but is defined by the accompanying claims. Within the scope of the application, it is self-evident that the through-bore for the tool, in particular for the drill wire, need not pass through the entire handpiece.

When using wires whose lengths do not exceed the length of the drive train, it is possible to provide a through-bore through only partial areas of the drive train. In addition, the bearing support of the driveless second shaft may be provided by a wide variety of forms of bearings, e.g., air bearings or friction bearings.

What is claimed is:

1. Medical or surgical handpiece for driving a medical tool, comprising:
    a housing; and
    a drive train accommodated in the housing, the drive train comprising a motor with a first drive shaft and a second shaft, the second shaft being at least partially arranged in the first drive shaft, wherein the second shaft is hollow and is mounted with at least one bearing to rotate freely relative to the first drive shaft so that the second shaft is rotatable independently of the first drive shaft, wherein the drive train further comprises a gear with a second output shaft, the gear being connected to the first drive shaft to drive the second output shaft at a rotational speed different from that of the first drive shaft.

2. Medical or surgical handpiece according to claim 1, wherein the first drive shaft is configured in two parts as a motor shaft and as a first output shaft.

3. Medical or surgical handpiece according to claim 1, further comprising at least one bearing to support the second shaft and wherein the at least one bearing is positioned within the drive train.

4. Medical or surgical handpiece according to claim 3, wherein the bearing is supported on one end of the drive train or of a shaft part of the drive train by a recess in the shaft wall.

5. Medical or surgical handpiece according to claim 1, further comprising at least one bearing to support the second shaft, and wherein the at least one bearing is supported on a rotationally fixed component of the handpiece.

6. Medical or surgical handpiece according to claim 5, wherein the bearing is accommodated in a housing opening arranged coaxially with the drive train.

7. Medical or surgical handpiece according to claim 5, wherein the drive train and the second shaft have a through-bore which passes through the handpiece.

8. Medical or surgical handpiece according to claim 1, wherein the at least one bearing is a roller bearing or a ball bearing.

9. Medical or surgical handpiece according to claim 1, wherein the second shaft is configured in two parts.

10. Medical or surgical handpiece according to claim 9, wherein the drive train and the second shaft have a through-bore which passes through the handpiece.

11. Medical or surgical handpiece according to claim 1, wherein the drive train and the second shaft have a through-bore which passes through the handpiece.

12. Medical or surgical handpiece for driving a medical tool, comprising:
    a housing; and
    a drive train accommodated in the housing, the drive train comprising a motor with a first drive shaft and a second shaft, the second shaft being at least partially arranged in the first drive shaft, wherein the second shaft is hollow and is mounted with at least one bearing to rotate freely relative to the first drive shaft so that the second shaft is rotatable independently of the first drive shaft,
    wherein the first drive shaft is configured in two parts as a motor shaft and as a first output shaft, and
    wherein the drive train further comprises a gear with a second output shaft, the gear being connected to the first drive shaft to drive the second output shaft at a rotational speed different from that of the first output shaft.

13. Medical or surgical handpiece according to claim 12, wherein the first output shaft extends at least partially through the second output shaft.

14. Medical or surgical handpiece, comprising:
    a housing; and
    a drive train accommodated in the housing, the drive train comprising a motor with a first drive shaft and a second shaft, the second shaft being at least partially arranged in the first drive shaft, wherein the second shaft is mounted with at least one bearing to rotate freely relative to the first drive shaft so that the second shaft is rotatable independently of the first drive shaft,
    wherein the drive train further comprises a gear with a second output shaft, the gear being connected to the first drive shaft to drive the second output shaft at a rotational speed different from that of the first drive shaft, and
    wherein the second shaft extends at least partially through the second output shaft.

15. Medical or surgical handpiece for driving a medical tool, comprising:
    a housing; and
    a drive train accommodated in the housing, the drive train comprising a motor with a first drive shaft and a second shaft, the second shaft being at least partially arranged in the first drive shaft, wherein the second shaft is hollow and is mounted with at least one bearing to rotate freely relative to the first drive shaft so that the second shaft is rotatable independently of the first drive shaft, wherein the drive train additionally has a coupling device to accommodate a tool or a surgical wire.

16. Medical or surgical handpiece according to claim 15, wherein the coupling device is detachable from the drive train.

* * * * *